(12) United States Patent
Maeda et al.

(10) Patent No.: US 7,102,531 B2
(45) Date of Patent: Sep. 5, 2006

(54) REMOTE CONTROLLER FOR TELEVISION/VIDEO RECORDER HAVING A FUNCTION OF MEASURING BODY FAT AND BODY FAT METER

(75) Inventors: Osamu Maeda, Daito (JP); Shinji Yoshida, Daito (JP); Katsuhiro Morisada, Daito (JP)

(73) Assignee: Funai Electric Co., Ltd., Daito (JP)

( * ) Notice: Subject to any disclaimer, the term of this patent is extended or adjusted under 35 U.S.C. 154(b) by 822 days.

(21) Appl. No.: 10/273,362

(22) Filed: Oct. 18, 2002

(65) Prior Publication Data
US 2003/0088188 A1    May 8, 2003

(30) Foreign Application Priority Data
Oct. 29, 2001  (JP) .............................. 2001-7044 U

(51) Int. Cl.
G08C 19/00  (2006.01)
H04N 5/44  (2006.01)
G01R 27/02  (2006.01)
G01R 27/08  (2006.01)
A61B 5/05  (2006.01)

(52) U.S. Cl. .................... 340/825.72; 340/825.71; 600/547; 348/734; 324/692; 324/611

(58) Field of Classification Search ................ 600/547; 340/825.72, 825.71; 348/734; 324/692, 324/611
See application file for complete search history.

(56) References Cited

U.S. PATENT DOCUMENTS
6,906,533 B1 *  6/2005  Yoshida ...................... 324/692
2001/0034491 A1  10/2001  Benson et al.

FOREIGN PATENT DOCUMENTS
CN   1310982 A   9/2001
JP   11-178804   7/1999

* cited by examiner

*Primary Examiner*—Jeffery Hofsass
*Assistant Examiner*—Scott Au
(74) *Attorney, Agent, or Firm*—Crowell & Moring LLP

(57) ABSTRACT

A remote controller for a television/video recorder having a function of measuring a body fat includes a display section for displaying a measurement of the body fat and a message questioning whether or not a user to be examined carries a specific medical device such as a pacemaker, a reply entry section for entering a reply to the message, and a control section for controlling the action of a body fat meter. The control section directs the display section to display the message prior to the measurement of the body fat. Then, when receiving from the reply entry section a reply indicating that the user carries a pacemaker, the control section inhibits the measurement of the body fat and directs the display section to display a message of the inhibition. When receiving from the reply entry section a reply indicating that the user carries no pacemaker, the control section enables the measurement of the body fat of the user through registering the physical data including the weight and the height of the user. This safety feature can thus protect and hold the user who carries a specific medical device such as a pacemaker in the safety.

10 Claims, 7 Drawing Sheets

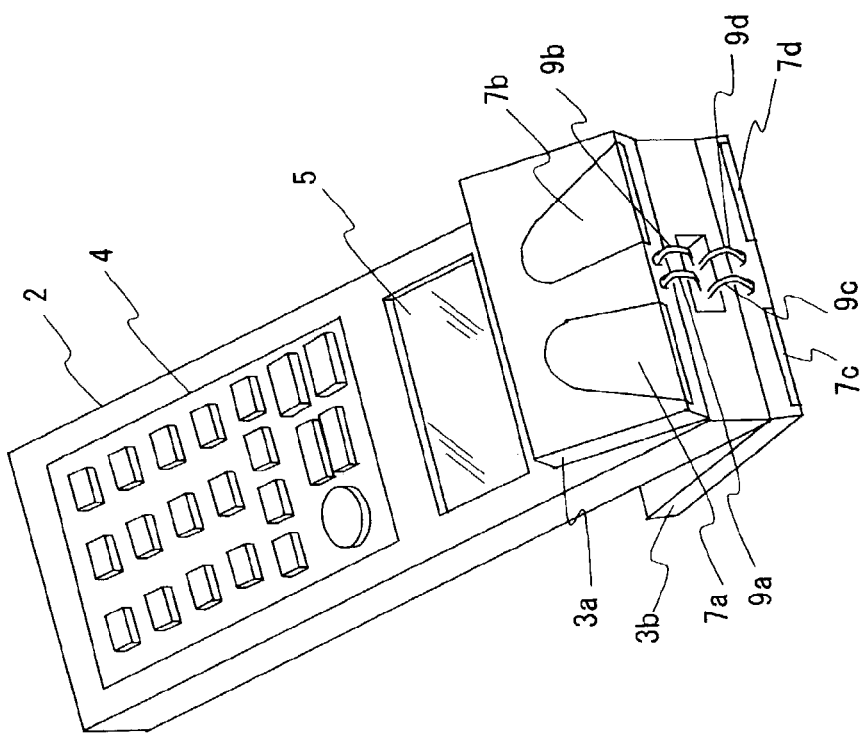
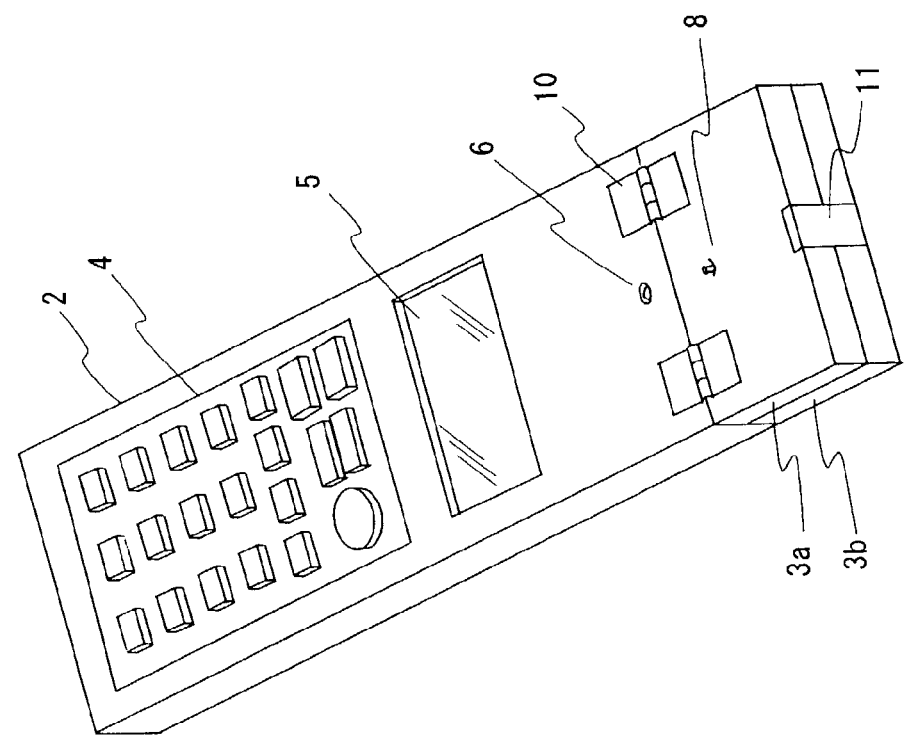

REMOTE CONTROLLER FOR TELEVISION/VIDEO RECORDER HAVING A FUNCTION OF MEASURING BODY FAT AND BODY FAT METER

BACKGROUND OF THE INVENTION

The present invention relates to a body fat meter equipped remote controller for a television/video recorder and a body fat meter arranged for measuring the impedance in the body of a subject to be measured and calculating the body fat of the subject from measurements of the impedance and physical data including the weight and the height of the subject.

In general, some body fat meters of such an impedance measurement type have been introduced which can measure the impedance in the body of a subject and calculate the body fat of the subject from measurements of the impedance and physical data including the weight and the height of the subject. More specifically, each of the conventional body fat meters for measuring the impedance in the body of a subject is designed for feeding a very small level of electric current between a pair of electrodes across the body of the subject and detecting an electric signal generated by the current running across the body of the subject to measure the impedance in the body. Then, the body fat of the subject is determined from the measurement of the impedance and the physical data including the weight and the height of the subject which are separately measured or have been recorded.

It is essential for measuring the impedance in the body of a subject with the conventional body fat meter of such an impedance measurement type to feed a very small level of the measuring current across the body of a subject to be measured. Although it is very small, the measuring current may cause some malfunctions of a specific medical device such as a pacemaker carried by the user thus resulting in the serious or fatal incident. For the safety of its user who carries a specific medical device such as a pacemaker, the conventional body fat meter comes with a safe-use notice printed directly on its outer surface or on its operation manual.

Another type of the conventional body fat meter for checking the number of pulses and measuring the body fat is known where the feeding of a small electric current across the body of a subject is systematically canceled when the subject is judged that its health condition is unfavorable for measurement of the body fat (as disclosed, for example, in Japanese Patent Laid-open Publication HEI 11-178804).

Such a safety-use notice printed on the outer surface or the operation manual of the conventional body fat meter is simply a warning but not a positive safety measure. In case that the user carrying a specific medical device such as a pacemaker fails to check the notice printed on the outer surface or read the operation manual, it may switch on the body fat meter for measuring the body fat and hence expose itself to a risk of having a serious or fatal incident. Also, the teaching disclosed in Japanese Patent Laid-open Publication HEI 11-178804 may hardly eliminate the above drawback.

SUMMARY OF THE INVENTION

The present invention has been developed for eliminating the above drawback and its object is to provide a body fat meter equipped remote controller for a television/video recorder and a body fat meter where any user who carries a specific medical device such as a pacemaker can be protected with an improved safety feature and securely held in the safety.

According to an aspect of the present invention, a remote controller for a television/video recorder having a function of measuring a body fat which is capable of selecting a desired receiving/recording channel of the television broadcasting, comprises: an electrode section including a pair of current electrodes which feed a current across the body of a user to be examined for the body fat and a pair of measurement electrodes which detect an electric signal generated by the current being fed across the body of the user; an impedance measuring circuit which feeds the current between the current electrodes of the electrode section and measures an impedance across the body of the user to determine the body fat of the user from the electric signal detected by the measurement electrodes; a physical data setting section which is operated by the user for registering physical data including the weight, the height, the sex, and the age of the user; a body fat calculator which calculates the body fat of the user from the impedance across the body of the user measured by the impedance measuring circuit and the physical data of the user registered by the physical data setting section; a display which displays a resultant measurement of the body fat calculated by the body fat calculator and a message questioning whether or not the user carries a medical device including a pacemaker; a reply entry section operated by the user for entering a reply to the message; and a control section which directs the display to display the message prior to the measurement of the body fat of the user, inhibits the measurement of the body fat when a reply is received from the reply entry section indicating that the user carries a specific medical device including a pacemaker, and enables the measurement of the body fat when a reply is received from the reply entry section indicating that the user carries non of a specific medical device including a pacemaker.

In this invention, it is examined whether or not the user to be examined for the body fat carries a specific medical device such as a pacemaker prior to the measurement of the body fat. When a reply is received indicating that the user carries a specific medical device such as a pacemaker, the measurement of the body fat of the user is inhibited. When a reply is received indicating that the user carries non of a specific medical device such as a pacemaker, the measurement of the body fat is enabled. As the physical data including the weight and the height of the user have been registered, the impedance across the body of the user is measured and then the body fat of the user is calculated from the physical data of the user and the impedance across the body and displayed on the remote controller. This allows every user to check the message questioning whether or not the user carries a specific medical device such as a pacemaker whenever he or she wants to measure the body fat and make a reply to the message. When a reply is made indicating that the user carries a specific medical device such as a pacemaker, the measurement of the body fat of the user is inhibited. Accordingly, any user who carries a specific medical device such as a pacemaker can be informed of a risk of the measurement of the body fat when such a pacemaker is carried and thus protected with a sort of improved safety feature. While the measurement of the body fat is disabled, the remote controller can be used for selecting a desired channel of the TV broadcasting service or the video recording system.

According to another aspect of the present invention, a remote controller for a television/video recorder having a function of measuring a body fat which is capable of selecting a desired receiving/recording channel of the television broadcasting, comprises: a transmitter which transmits to a television receiver a body fat measurement command signal which includes the impedance across the body measured by the impedance measuring circuit and the physical data registered by the physical data setting section so that the body fat of the user to be examined can be calculated in the television receiver; a message display which displays a message questioning whether or not the user carries a medical device including a pacemaker; a reply entry section operated by the user for entering a reply to the message; and a control section which directs the message display to display the message prior to the measurement of the body fat of the user, inhibits the measurement of the body fat when a reply is received from the reply entry section indicating that the user carries a specific medical device including a pacemaker, and enables the measurement of the body fat when a reply is received from the reply entry section indicating that the user carries non of a specific medical device including a pacemaker.

In this invention, it is examined whether or not the user to be examined for the body fat carries a specific medical device such as a pacemaker prior to the measurement of the body fat. When a reply is received indicating that the user carries a specific medical device such as a pacemaker, the measurement of the body fat of the user is inhibited. When a reply is received indicating that the user carries non of a specific medical device such as a pacemaker, the measurement of the body fat is enabled. As the physical data including the weight and the height of the user have been registered, the impedance across the body of the user is measured. The physical data and the impedance data are then transmitted to a television receiver where they are used for calculating the body fat of the user. A calculation of the body fat is displayed on the television receiver. While the measurement of the body fat is disabled, the remote controller can be used for selecting a desired channel of the TV broadcasting service or the video recording system.

According to still another aspect of the present invention, a body fat meter having a body fat calculator which calculates the body fat of the user from the impedance across the body of the user measured by the impedance measuring circuit and the physical data of the user registered by the physical data setting section, comprising: a message display which displays a message questioning whether or not the user carries a medical device including a pacemaker; a reply entry section operated by the user for entering a reply to the message; and a control section which directs the message display to display the message prior to the measurement of the body fat of the user, inhibits the measurement of the body fat when a reply is received from the reply entry section indicating that the user carries a specific medical device including a pacemaker, and enables the measurement of the body fat when a reply is received from the reply entry section indicating that the user carries non of a specific medical device including a pacemaker.

In this invention, it is examined whether or not the user to be examined for the body fat carries a specific medical device such as a pacemaker prior to the measurement of the body fat. When a reply is received indicating that the user carries a specific medical device such as a pacemaker, the measurement of the body fat of the user is inhibited. When a reply is received indicating that the user carries non of a specific medical device such as a pacemaker, the measurement of the body fat is enabled.

BRIEF DESCRIPTION OF THE DRAWINGS

FIGS. 1A and 1B are perspective views of a body fat meter equipped remote controller showing one embodiment of the present invention;

DETAILED DESCRIPTION OF THE PREFERRED EMBODIMENTS

Figure 2:
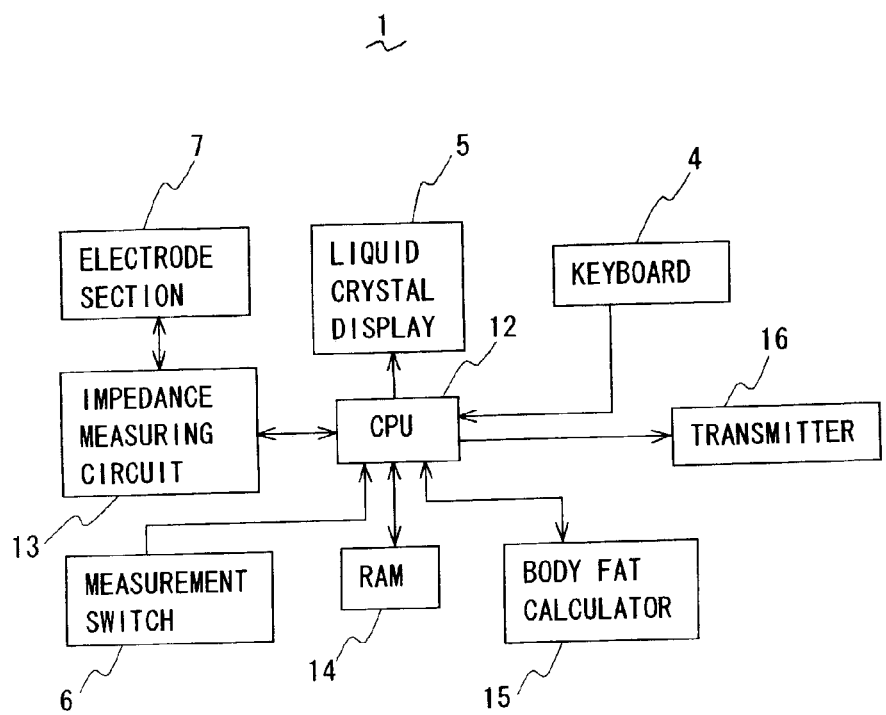
FIG. 2 is a block diagram showing an electrical arrangement of the remote controller.

Some embodiments of the present invention will be described referring to the relevant drawings. FIGS. 1A and 1B illustrate a remote controller equipped with a body fat meter according to a first embodiment of the present invention. The body fat meter equipped remote controller 1 has a function of measuring the body fat of a user while carrying out a remote control action for selecting any desired channel of the existing television broadcast service and comprises a main unit 2 and a couple of openable sections 3a and 3b.

The main unit 2 includes a keyboard 4 (physical data setting and reply entry section), a liquid crystal display 5 (body fat measurement display and message display), and a measurement switch 6. The openable section 3a has a projection 8 provided on the outer side thereof and a pair of current electrodes 7a and 7b provided on the inner side thereof for feeding a current to measure the impedance in the body. The openable section 3b has a pair of measurement electrodes 7c and 7d provided on the inner side thereof for measuring the impedance in the body while a current flowing to a user's body by the current electrodes 7a and 7b. The current electrodes 7a and 7b and the measurement electrodes 7c and 7d are electrically connected by electric cables 9a, 9b, 9c, and 9d respectively to the main unit 2.

The openable sections 3a and 3b are located on this side of the remote controller 1 when it is in use and joined by hinges 10 to the main unit 2 for opening and closing. The openable sections 3a and 3b remain urged by spring means, not shown, for opening towards the upper and the lower respectively and closed together with a stopper 11. When the stopper 11 is unlocked, the two openable sections 3a and 3b are turned to their half open state by the yielding force of the spring means. As the openable section 3a is shifted from the half open state to the fully open state, its projection 8 presses against the measurement switch 6 on the main body 2. With the two openable sections 3a and 3b remaining open, the current electrodes 7a and 7b and the measurement electrodes 7c and 7d are exposed at this side of the remote controller 1 when it is in use.

When the body fat meter equipped remote controller 1 is used for not measuring the body fat, its two openable sections 3a and 3b remain closed with the current electrodes 7a and 7b and the measurement electrodes 7c and 7d not exposed. For measuring the body fat, the stopper 11 is unlocked to open the two openable sections 3a and 3b. This allows the current electrodes 7a and 7b and the measurement electrodes 7c and 7d to be exposed for starting the measurement of the impedance in the body. More particularly, while the current electrode 7a and the measurement electrode 7c are held directly by the fingers of one hand (at the left) of the user, the current electrode 7b and the measurement electrode 7d are engaged directly with the fingers of the other hand (at the right). As the two openable sections 3a and 3b remain at their fully open state, the measurement switch 6 is turned on by the pressing action of the projection 8 of the openable section 3a for feeding a current between the current electrodes 7a and 7b. As the result, the impedance in the body of the user can be measured.

FIG. 2 is an electrical block diagram of the body fat meter equipped remote controller 1 of this embodiment. The body fat meter equipped remote controller 1 includes a CPU 12 (a control section) for controlling the actions of the remote controller 1. The CPU 12 is connected to an impedance measuring circuit 13, a RAM 14, a body fat calculator 15, and a transmitter 16 as well as the keyboard 4, the liquid crystal display 5, and the measurement switch 6. The impedance measuring circuit 13 is also connected to an electrode section 7 which consists mainly of the current electrodes 7a and 7b and the measurement electrodes 7c and 7d.

The keyboard 4 switches between a TV control mode for selecting a desired channel of the existing TV broadcasting service and a body fat measurement mode for measuring the body fat of a user. In the TV control mode, the action is carried out for selecting a desired TV channel. In the body fat measurement mode, the entry of physical data of the user including the weight, the height, the sex, and the age is carried out as well as the entry of information whether or not the user carries a specific medical device such as a pacemaker. When the entry actions are conducted at the keyboard 4, their corresponding signals are transferred to the CPU 12.

The liquid crystal display 5 is controlled by the CPU 12 for displaying the information whether the user carries a pacemaker or not as a message form and the physical data of the user including the weight, the height, the sex, and the age received from the keyboard 4 in addition to a measurement of the body fat. The information whether or not the user carries a pacemaker may be expressed by a message "Do you have a pacemaker? 1. yes 2. no". As the electrode section 7 consists mainly of the current electrodes 7a and 7b and the measurement electrodes 7c and 7d, the impedance across the body of the user can be measured by the user touching at one hand the current electrode 7a and the measurement electrode 7c and at the other hand the current electrode 7b and the measurement electrode 7d.

The measurement switch 6 is turned on when pressed down with the projection 8 and its ON signal is received by the CPU 12. The impedance measuring circuit 13 is controlled by the CPU 12 for feeding a current between the current electrodes 7a and 7b of the electrode section 7 and measuring the voltage level between the measurement electrodes 7c and 7d to determine the impedance across the body of the user. The impedance determined by the impedance measuring circuit 13 is then transferred to the CPU 12.

The RAM 14 is controlled by the CPU 12 for saving the physical data including the weight, the height, the sex, and the age of the user entered from the keyboard 4 and the impedance determined by the impedance measuring circuit 13. The body fat calculator 15 is controlled by the CPU 12 for calculating the body fat of the user from the impedance and the physical data including the weight, the height, the sex, and the age. The transmitter 16 is controlled by the CPU 12 for transmitting selection signals, e.g. for selecting the desired TV channel, and control signals in the form of infrared ray signals to the television receiver.

Figure 3:
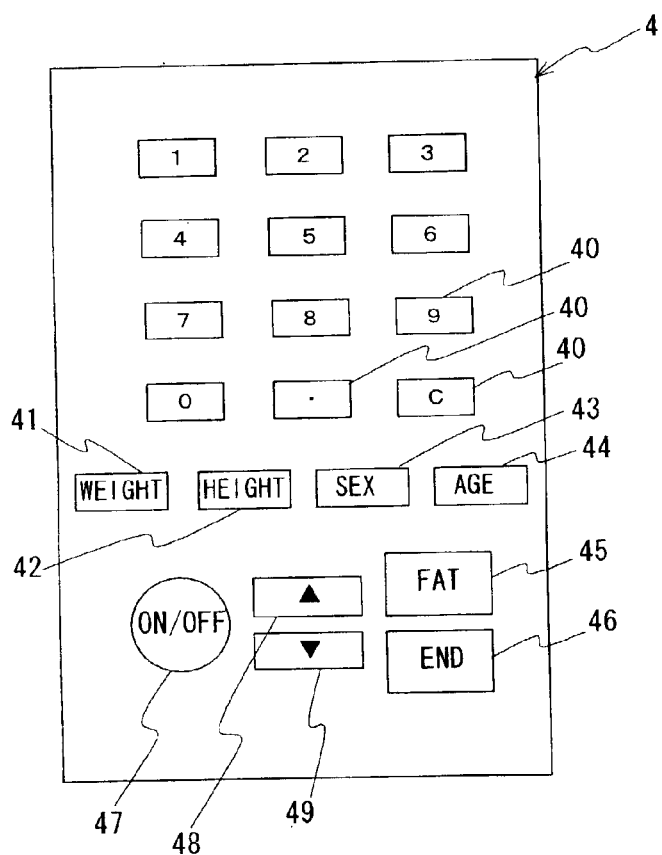
FIG. 3 is a view showing a keyboard of the remote controller.

As best shown in FIG. 3, the keyboard 4 includes a set of numerical entry keys 40, a weight entry key 41, a height entry key 42, a sex entry key 43, an age entry key 44, a FAT key 45, and an end key 46. The keyboard 4 also includes a power on key 47 for turning the television receiver on and off and a couple of sound keys 48 and 49 for adjusting the sound level of the television receiver.

The FAT key 45 is actuated for shifting from the TV control mode to the body fat measurement mode. The end key 46 is actuated for stopping the body fat measurement mode and returning back to the TV control mode. The numerical entry keys 40 are actuated for selecting a desired channel of the TV broadcasting service, determining whether or not the user carries a pacemaker, and entering the physical data of the user including the weight, the height, the sex, and the age. For determining whether or not the user carries a pacemaker, the liquid crystal display 5 displays the message "Do you have a pacemaker? 1. yes, 2. no". Then, the involvement of a pacemaker is registered by pressing the numerical key 40 printed with "1". Otherwise, no involvement of a pacemaker is registered by pressing the numerical key 40 printed with "2". The physical data of the user are registered by pressing any of the weight entry key 41, the height entry key 42, the sex entry key 43, and the age entry key 44 and entering its corresponding number with the numerical keys 40.

In response to the signal from the keyboard 4, the CPU 12 switches between the TV control mode for selecting a desired channel of the TV broadcasting service and the body fat measurement mode for measuring the body fat of the user. When the TV control mode is selected, the CPU 12 allows the keyboard 4 to enter a desired channel of the TV broadcasting service. As the desired channel is selected by the action of the keyboard 4, its signal is released from the transmitter 16.

When the body fat measurement mode is selected, the CPU 12 drives the liquid crystal display 5 to display the message questioning whether or not the user carries a pacemaker and wait for a reply made by the user operating the keyboard 4. When receiving a reply indicating that the user carries a pacemaker, the CPU 12 drives the liquid crystal display 5 to display a message indicating that the measurement of the body fat is inhibited and switches back to the TV control mode. When receiving a reply indicating that the use carries no pacemaker, the CPU 12 proceeds the measurement of the body fat and allows the user to register its physical data including the weight, the height, the sex, and the age from the keyboard 4.

Upon receiving the start signal from the measurement switch 6 when the measurement of the body fat is enabled, the CPU 12 supplies the measuring circuit 13 with a command for starting the feeding of a current between the two current electrodes 7a and 7b of the electrode section 7. As the result, the measuring circuit 13 starts measuring the impedance in the body of the user. Then, the CPU 12 drives the body fat calculator 15 to calculate the body fat from the impedance measured by the measuring circuit 13 and the physical data including the weight, the height, the sex, and the age registered from the keyboard 4 and displays a calculated result of the body fat on the liquid crystal display 5.

Figure 4:
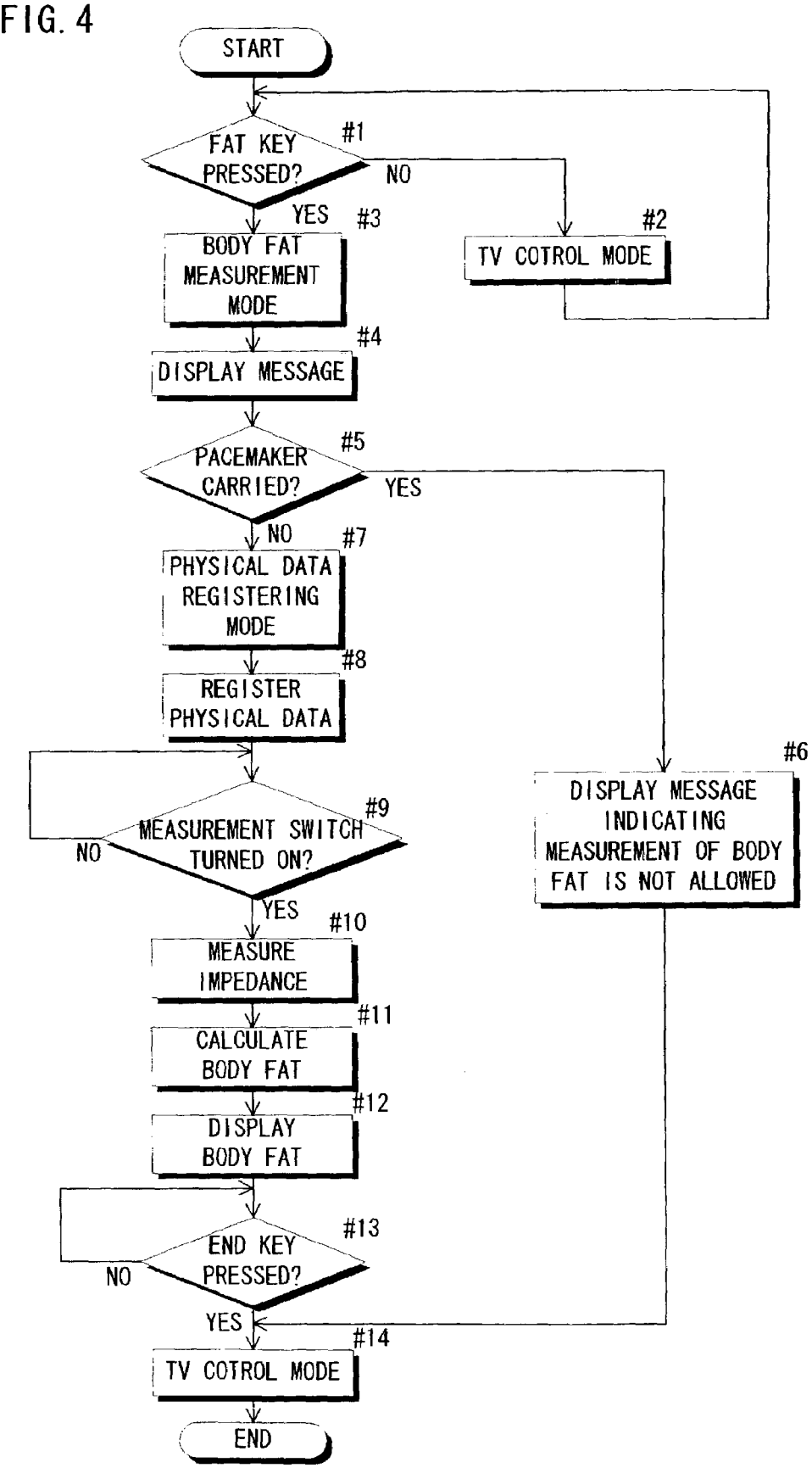
FIG. 4 is a flowchart showing a procedure of measuring the body fat with the remote controller.

A procedure of measuring the body fat with the body fat meter equipped remote controller 1 of the embodiment will now be explained referring to the flowchart of FIG. 4. The procedure starts with examining whether the FAT key 45 on the keyboard 4 is pressed down or not (#1). When the FAT key 45 is not pressed down (No at #1), the TV control mode for selecting a desired channel of the TV broadcasting service remains enabled (#2). When the FAT key 45 is pressed down (Yes at #1), the action is shifted to the body fat measurement mode for measuring the body fat (#3).

As the body fat measurement mode is enabled at the step #3, the message "Do you have a pacemaker? 1. yes, 2. no" is displayed on the liquid crystal display 5 of the remote controller 1 (#4). This allows the user to enter a reply to the message using "1" or "2" of the numerical keys 40 of the keyboard 4. When the numerical key 40 of "1" is pressed down, it is judged that the user carries a pacemaker. When the numerical key 40 of "2" is pressed down, it is judged that the user carries no pacemaker (#5).

When the remote controller 1 judges that the user carries a pacemaker (yes at #5), its liquid crystal display 5 displays the message indicating that the measurement of the body fat is not allowed (#6) and its action returns back to the TV control mode (#14). When the remote controller 1 judges that the user carries no pacemaker (no at #5), its action shifts to a mode of registering the physical data (#7) where the physical data including the weight, the height, the sex, and the age of the user can be registered using the keyboard 4.

As the mode of registering the physical data is enabled at the step #7, the weight, the height, the sex, and the age of the user are entered using the weight entry key 41, the height entry key 42, the sex entry key 43, and the age entry key 44 in combination with the numerical keys 40 of the keyboard 4. Those entries are registered as the physical data of the user in the remote controller 1 (#8). The remote controller 1 saves the physical data in the RAM 14 and simultaneously displays the same on the liquid crystal display 5 for the user checkup.

When the measurement switch 6 of the remote controller 1 is turned on with the openable sections 3 opened and the electrodes 7 held directly by the user (yes at #9), the current electrodes 7a and 7b of the electrode section 7 is fed with a measurement current for measuring the impedance across the body of the user (#10). After the measurement of the impedance, the remote controller 1 reads out the physical data from the RAM 14 and directs the body fat calculator 15 to calculate the body fat from the measured impedance and the physical data (#11). A calculation of the body fat is then displayed on the liquid crystal display 5 (#12). When the end key 46 of the keyboard 4 is pressed down (yes at #13), the action of the remote controller 1 shifts from the body fat measurement mode to the TV control mode (#14).

As described, the action of the body fat meter equipped remote controller 1 can simply be switched between the TV control mode and the body fat measurement mode with the use of its keyboard 4 for selecting a desired channel of the existing TV broadcasting service in the former mode and measuring the body fat of a user in the latter mode. In the body fat measurement mode, the message questioning whether the user whose body fat is to be examined carries a pacemaker or not is displayed on the liquid crystal display 5. When the user has a reply indicating that the user carries a pacemaker using the keyboard 4, the measurement of the body fat is inhibited and its message is displayed on the liquid crystal display 5. When the user has a reply indicating that the user carries no pacemaker, the body fat measurement is enabled and the physical data including the weight, the height, the sex, and the age of the user can be registered for measurement of the body fat. A resultant measurement of the body fat is then displayed on the liquid crystal display 5.

Figure 5:
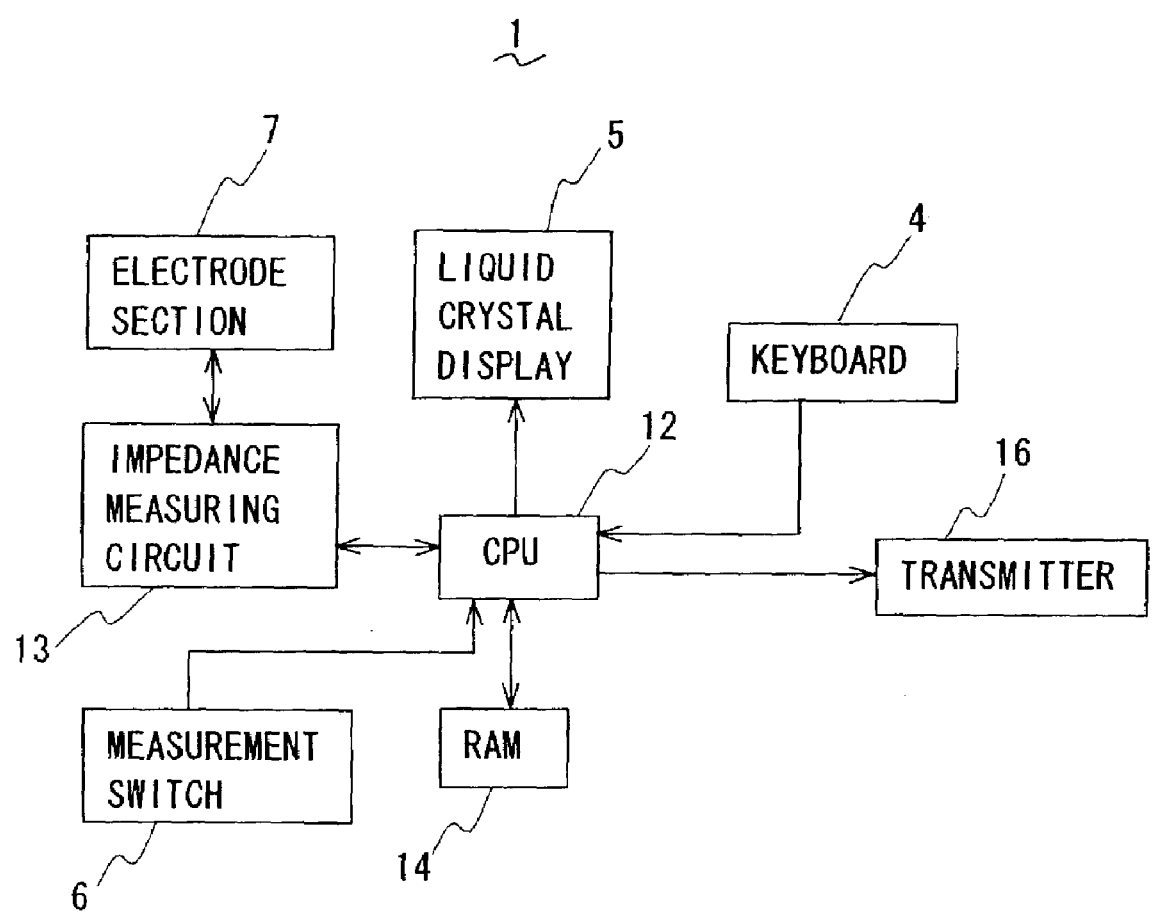
FIG. 5 is a block diagram of an electrical arrangement of a body fat meter equipped remote controller showing another embodiment of the present invention.

FIG. 5 is an electrical block diagram of another body fat meter equipped remote controller showing a second embodiment of the present invention. The body fat meter equipped remote controller 1 of the second embodiment is designed for remote controlling the selection of a desired channel in the existing TV broadcasting service while measuring the impedance across the body of a user to calculate the body fat of the user which is then displayed on a television receiver.

The remote controller 1 has a CPU 12 (a control section) for controlling the actions of the remote controller 1. The CPU 12 is electrically connected to a keyboard 4, a liquid crystal display 5, a measurement switch 6, an impedance measuring circuit 13, a RAM 14, and a transmitter 16. The impedance measuring circuit 13 is also connected to an electrode section 7 which consists mainly of a pair of current electrodes 7a and 7b and another pair of measurement electrodes 7c and 7d. The CPU 12 is arranged to transmit from the transmitter 16 to a television receiver a body fat measurement signal constructed from the physical data including the weight, the height, the sex, and the age of the user which are registered by the action of the keyboard 4 and the impedance across the body measured by the impedance measuring circuit 13 and an end signal indicating the end of the body fat measurement mode in the form of infrared ray signals. The other arrangement of the remote controller 1 of this embodiment is substantially identical to that of the previous embodiment.

Figure 6:
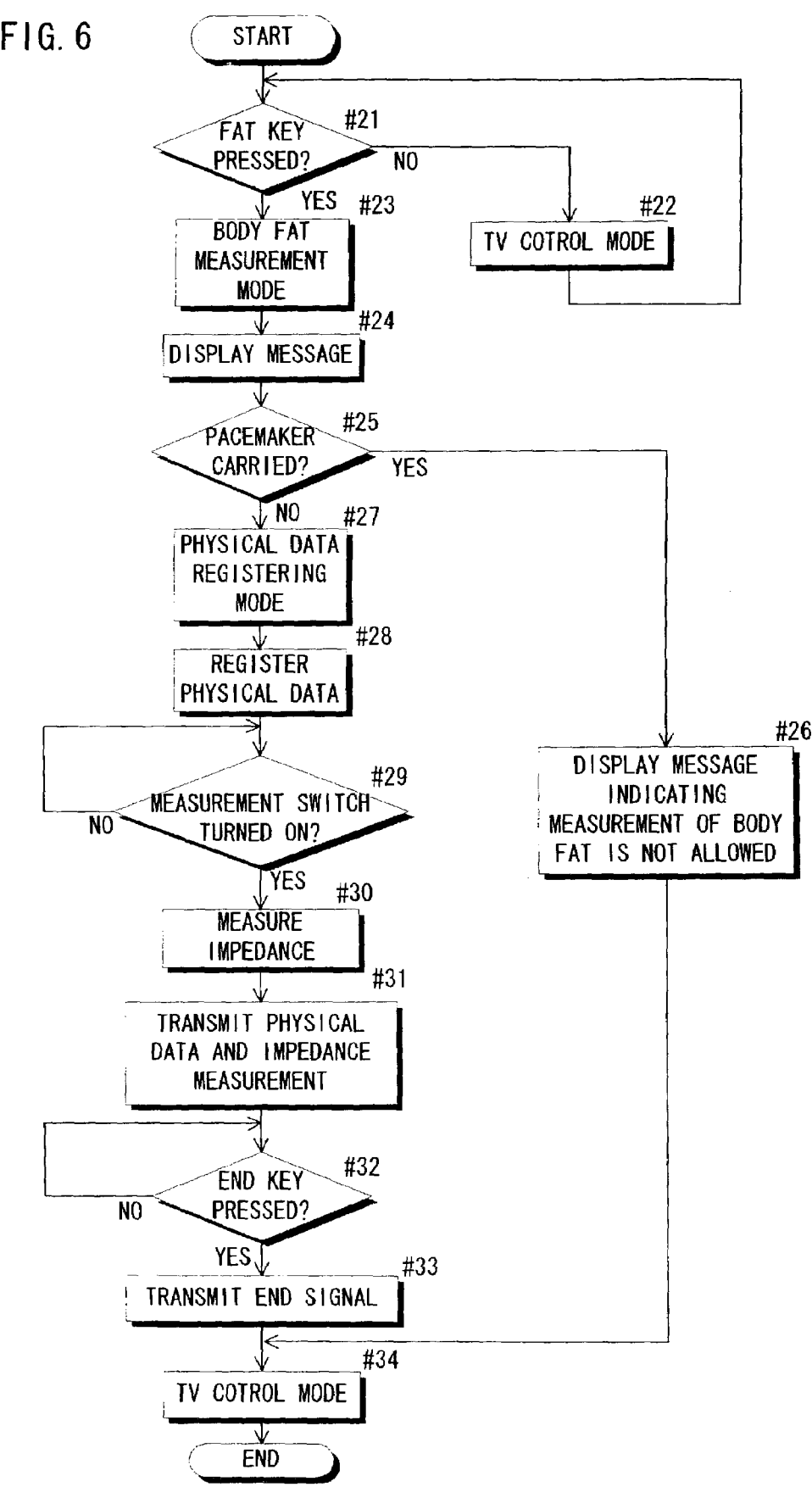
FIG. 6 is a flowchart showing a procedure of measuring the body fat with the another remote controller.

A procedure of measuring the body fat with the body fat meter equipped remote controller 1 of the second embodiment will now be explained referring to the flowchart of FIG. 6. The steps from #21 to #30 are equal to those of the previous embodiment. When the measurement of the impedance across the body has been completed at the step #29, the remote controller 1 reads out the physical data of the user from the RAM 14 and transmits a body fat measurement signal constructed from the physical data and a measurement of the impedance in the form of an infrared ray signal from the transmitter 16 to a television receiver (#31). Upon receiving the signal of the impedance and the physical data including the weight, the height, the sex, and the age of the user, the television receiver calculates and displays the body fat of the user. When the end key 46 of its keyboard 4 is pressed down (yes at #32), the remote controller 1 transmits an end signal indicating that the body fat measurement mode is canceled from the transmitter 16 to the television receiver (#33) and its action is shifted from the body fat measurement mode to the TV control mode (#34).

Figure 7:
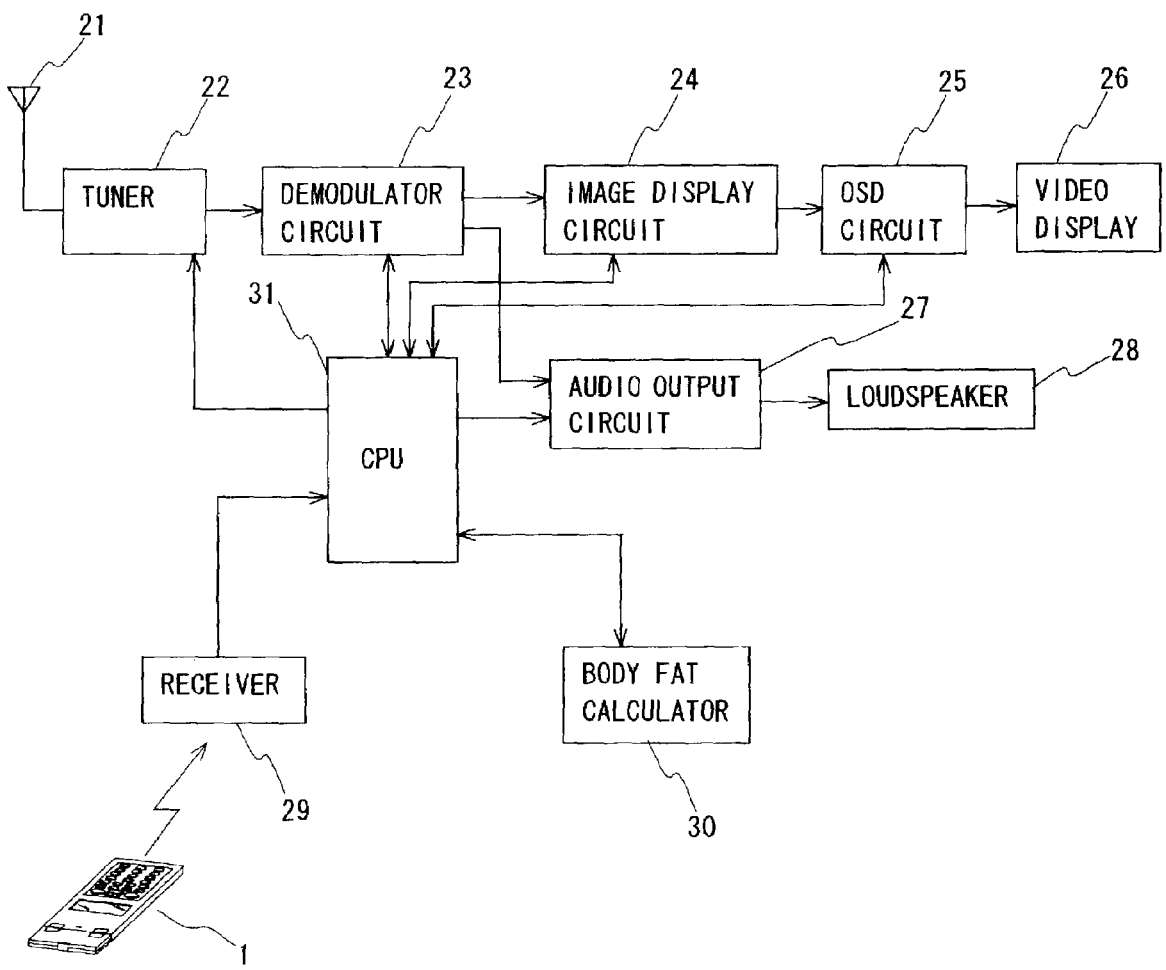
FIG. 7 is a block diagram of an electrical arrangement of a television receiver operated by the remote controller.

FIG. 7 is an electrical block diagram of the television receiver controlled by the body fat meter equipped remote controller 1 of this embodiment. The television receiver 20 has a function of calculating the body fat of the user from the body fat measurement signal received from the body fat meter equipped remote controller 1 and displaying a result of the body fat. The television receiver 20 comprises an antenna 21 for receiving TV broadcasting waves, a tuner 22, a demodulator circuit 23, an image display circuit 24, an OSD circuit 25, a video display 26 (body fat display), an audio output circuit 27, a loudspeaker 28, a receiver 29, and a body fat calculator 30.

In the television receiver 20, the tuner 22 is controlled by a CPU 34 to tune the frequency of a desired channel of the TV broadcasting service for receiving a high-frequency TV signal at the channel with the antenna 21. The high-frequency TV signal is then demodulated by the demodulator circuit 23 and reconstructed to a video signal by the image display circuit 24 and to an audio signal by the audio output circuit 27. The video signal reconstructed by the image display circuit 24 is transferred via the OSD circuit 25 to the video display 26 where an image of the channel of the TV broadcasting service is displayed. The audio signal reconstructed by the audio output circuit 27 is transferred to the loudspeaker 28 for emitting sounds of the channel of the TV broadcasting service. The receiver 29 is designed for receiving an infrared ray signal from the body fat meter equipped remote controller 1. The body fat calculator 30 calculates the body fat of a user from the impedance across the body and the physical data including the weight, the height, the sex, and the age of the user which have been received by the receiver 29.

In response to a TV command signal received by the receiver 29, the CPU 34 drives the tuner 22 to tune the frequency of a desired channel of the TV broadcasting service and the video display 26 to display an image of the desired channel along with its corresponding sound emitted from the loudspeaker 28. When the receiver 29 receives a command for measuring the body fat, the CPU 34 directs the measurement of the impedance and the display of the body fat.

Figure 8:
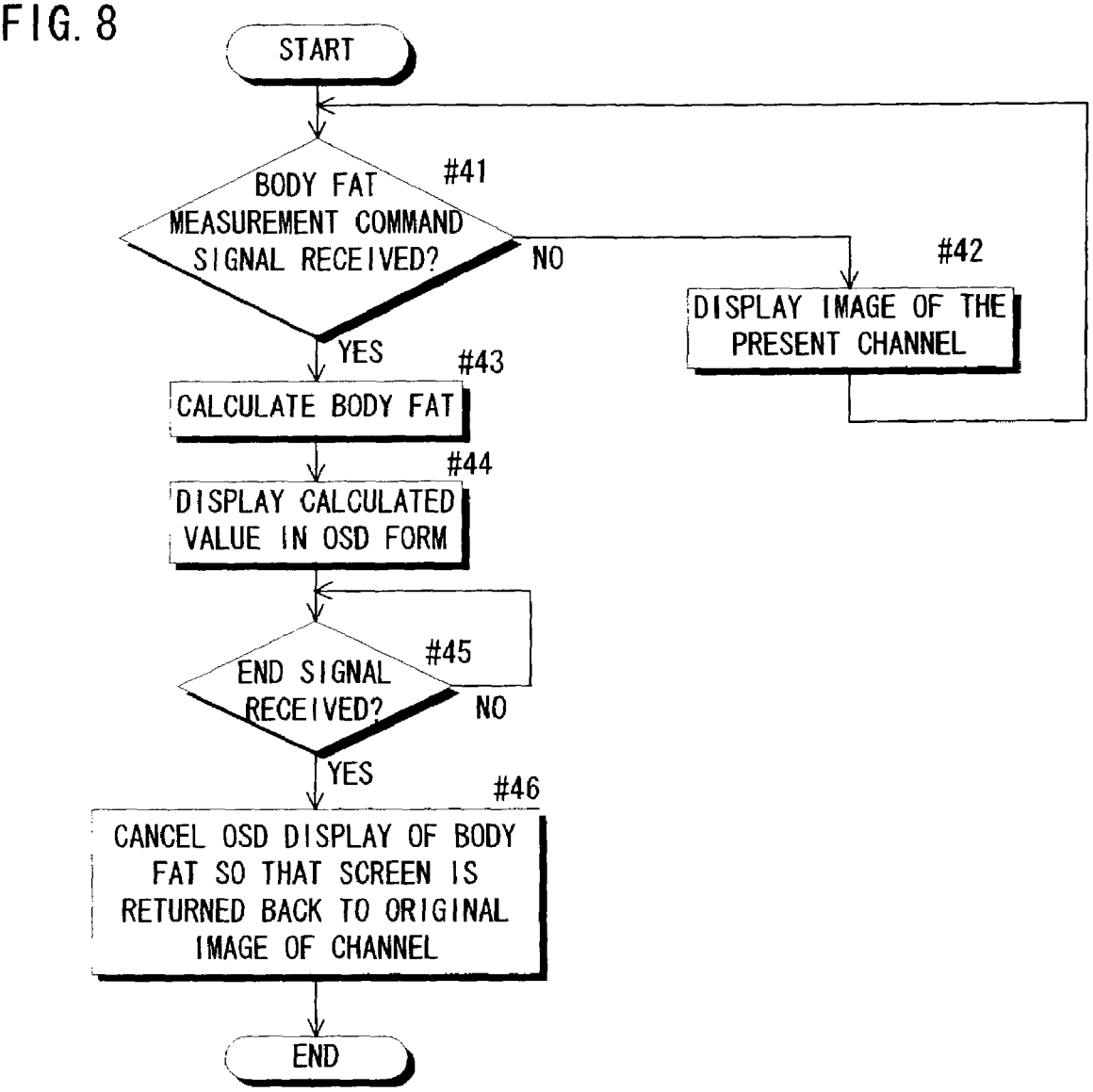
FIG. 8 is a flowchart showing a procedure of measuring the body fat with the television receiver operated by the remote controller.

A procedure of measuring and displaying the body fat on the TV receiver 20 will be explained referring to the flowchart of FIG. 8. The procedure starts with the TV receiver 20 examining whether or not the body fat measurement command signal is received (#41). When the body fat measurement command signal is not received (no at #41), a common action of displaying an image of the present channel of the TV broadcasting service is conducted (#42). When the body fat measurement command signal is received (yes at #41), the body fat of a desired user is calculated by the body fat calculator 30 from the impedance measured by the remote controller and the physical data including the weight, the height, the sex, and the age of the user (#43) and its calculated value is displayed in an OSD form over the image of the present channel of the TV broadcasting service on the video display 26 (#44). When the end signal is received by the TV receiver 20 (yes at #45), the OSD display of the body fat is canceled on the video display 26 and the screen is returned back to the original image of the channel of the TV broadcasting service (#46).

The body fat meter equipped remote controller 1 of this embodiment having the foregoing arrangement, like that of the first embodiment, allows the body fat of a user to be measured while a desired channel of the TV broadcasting service can be selected. Prior to the measurement of the body fat, the message questioning whether or not the user carries a specific medical device such as a pacemaker is displayed. When a reply indicates that the user carries a specific medical device such as a pacemaker, the measurement of the body fat is inhibited and its inhibition is displayed. When it is replied that the user carries non of a specific medical device such as a pacemaker, the measurement of the body fat is enabled through registering the physical data including the weight, the height, the sex, and the age of the user. Using the body fat meter equipped remote controller 1 of this embodiment, a resultant measurement of the body fat of the user can be displayed on the screen of a television receiver.

The present invention is not limited to the above embodiments but may be modified to desired forms. For example, the body fat meter equipped remote controller of the present invention may be a video recorder remote controller for selecting and controlling a desired channel of the video recording system. Also, the body fat meter is not limited to an extra function of a remote controller but may be a commercially available single-purpose product where it is examined prior to the measurement of the body fat of a user whether or not the user carries a specific medical device such as a pacemaker and when a reply is received indicating that the user carries a specific medical device such as a pacemaker, the measurement of the body fat is inhibited and when a reply is received indicating that the user carries non of a specific medical device such as a pacemaker, the measurement of the body fat is enabled. This application shall have a priority on the basis of Japanese utility model application No. 2001-7044 filed on Oct. 29, 2001. The teachings of the Japanese utility model application are to be fully covered by this application.

What is claimed is:

1. A remote controller for a television/video recorder having a function of measuring a body fat which is capable of selecting a desired receiving/recording channel of the television broadcasting, comprising:

an electrode section including a pair of current electrodes which feed a current across the body of a user to be examined for the body fat and a pair of measurement electrodes which detect an electric signal generated by the current being fed across the body of the user;

an impedance measuring circuit which feeds the current between the current electrodes of the electrode section and measures an impedance across the body of the user to determine the body fat of the user from the electric signal detected by the measurement electrodes;

a physical data setting section which is operated by the user for registering physical data including the weight, the height, the sex, and the age of the user;

a body fat calculator which calculates the body fat of the user from the impedance across the body of the user measured by the impedance measuring circuit and the physical data of the user registered by the physical data setting section;

a display which displays a resultant measurement of the body fat calculated by the body fat calculator and a message questioning whether or not the user carries a medical device including a pacemaker;

a reply entry section operated by the user for entering a reply to the message; and a control section which directs the display to display the message prior to the measurement of the body fat of the user, inhibits the measurement of the body fat when a reply is received from the reply entry section indicating that the user carries a specific medical device including a pacemaker, and enables the measurement of the body fat when a reply is received from the reply entry section indicating that the user carries non of a specific medical device including a pacemaker.

2. A remote controller for a television/video recorder having a function of measuring a body fat according to claim 1, wherein when receiving from the reply entry section the reply indicating that the user carries a specific medical device including a pacemaker, the control section directs the display to display a message indicating that the measurement of the body fat is inhibited.

3. A remote controller for a television/video recorder having a function of measuring a body fact according to claim 1, wherein when receiving from the reply entry section the reply indicating that the user carries non of a specific medical device including a pacemaker, the control section allows the registration of the physical data including the weight, the height, the sex, and the age of the user to be examined.

4. A remote controller for a television/video recorder having a function of measuring a body fat which is capable of selecting a desired receiving/recording channel of the television broadcasting, comprising:
　an electrode section including a pair of current electrodes which feed a current across the body of a user to be examined for the body fat and a pair of measurement electrodes which detect an electric signal generated by the current being fed across the body of the user;
　an impedance measuring circuit which feeds the current between the current electrodes of the electrodes section and measures and impedance across the body of the user to determine the body fat of the user from the electric signal detected by the measurement electrodes;
　a physical data setting section which is operated by the user for registering physical data including the weight, the height, the sex, and the age of the user;
　a transmitter which transmits to a television receiver a body fat measurement command signal which includes the impedance across the body measured by the impedance measuring circuit and the physical data registered by the physical data setting section so that the body fat of the user to be examined can be calculated in the television receiver;
　a message display which displays a message questioning whether or not the user carries a medical device including a pacemaker;
　a reply entry section operated by the user for entering a reply to the message; and
　a control section which directs the message display to display the message prior to the measurement of the body fat of the user, inhibits the measurement of the body fat when a reply is received from the reply entry section indicating that the user carries a specific medical device including a pacemaker, and enables the measurement of the body fat when a reply is received from the reply entry section indicating that the user carries non of the specific medical device including a pacemaker.

5. A remote controller for a television/video recorder having a function of measuring a body fat according to claim 4, wherein when receiving from the reply entry section the reply indicating that the user carries a specific medical device including a pacemaker, the control section directs the message display to display a message indicating that the measurement of the body fat is inhibited.

6. A remote controller for a television/video recorder having a function of measuring a body fat according to claim 4, wherein when receiving from the reply entry section the reply indicating that the user carries non of a specific medical device including a pacemaker, the control section allows the registration of the physical data including the weight, the height, the sex, and the age of the user to be examined.

7. A body fat meter having an electrode section including a pair of current electrodes which feed a current across the body of a user to be examined for the body fat and a pair of measurement electrodes which detect an electric signal generated by the current being fed across the body of the user, an impedance measuring circuit which feeds the current between the current electrodes of the electrode section and measures and impedance across the body of the user to determine the body fat of the user from the electric signal detected by the measurement electrodes, a physical data setting section which is operated by the user for registering physical data including the weight, the height, the sex, and the age of the user, and a body fat calculator which calculates the body fat of the user from the impedance across the body of the user measured by the impedance measuring circuit and the physical data of the user registered by the physical data setting section comprising:
　a message display which displays a message questioning whether or not the user carries a medical device including a pacemaker;
　a reply entry section operated by the user for entering a reply to the message; and
　a control section which directs the message display to display the message prior to the measurement of the body fat of the user, inhibits the measurement of the body fat when a reply is received from the reply entry section indicating that the user carries a specific medical device including a pacemaker, and enables the measurement of the body fat when a reply is received from the reply entry section indicating that the user carries non of a specific medical device including a pacemaker.

8. A body fat meter according to claim 7, wherein when receiving from the reply entry section the reply indicating that the user carries a specific medical device including a pacemaker, the control section directs the message display to display a message indicating that the measurement of the body fat is inhibited.

9. A body fat meter according to claim 7, wherein when receiving from the reply entry section the reply indicating that the user carries non of a specific medical device including a pacemaker, the control section allows the registration of the physical data including the weight, the height, the sex, and the age of the user to be examined.

10. A body fat meter having an electrode section including a pair of current electrodes which feed a current across the body of a user to be examined for the body fat and a pair of measurement electrodes which detect an electric signal generated by the current being fed across the body of the user, an impedance measuring circuit which feeds the current between the current electrodes of the electrode section and measures and impedance across the body of the user to determine the body fat of the user from the electric signal detected by the measurement electrodes, a physical data setting section which is operated by the user for registering physical data including the weight, the height, the sex, and the age of the user, and a body fat calculator which calculates the body fat of the user from the impedance across the body of the user measured by the impedance measuring circuit and the physical data of the user registered by the physical data setting section comprising:
　a message display which displays a message questioning whether or not the user carries a medical device including a pacemaker;
　a reply entry section operated by the user for entering a reply to the message;
　a control section which directs the message display to display the message prior to the measurement of the body fat of the user, inhibits the measurement of the body fat when a reply is received from the reply entry section indicating that the user carries a specific medical device including a pacemaker, and enables the measurement of the body fat when a reply is received from the reply entry section indicating that the user carries non of a specific medical device including a pacemaker; and
　further comprising a body fat measurement display which displays a measurement of the body fat calculated by the body fat calculator, the body fat measurement display also serving as the message display.

* * * * *